United States Patent
Panzner

(10) Patent No.: US 6,713,533 B1
(45) Date of Patent: Mar. 30, 2004

(54) NANOCAPSULES AND METHOD OF PRODUCTION THEREOF

(75) Inventor: Steffen Panzner, Halle (DE)

(73) Assignee: Novosom AG, Halle (DE)

(*) Notice: Subject to any disclaimer, the term of this patent is extended or adjusted under 35 U.S.C. 154(b) by 0 days.

(21) Appl. No.: 09/831,975

(22) PCT Filed: Nov. 15, 1999

(86) PCT No.: PCT/EP99/09744
§ 371 (c)(1),
(2), (4) Date: May 16, 2001

(87) PCT Pub. No.: WO00/28972
PCT Pub. Date: May 25, 2000

(30) Foreign Application Priority Data

Nov. 17, 1998 (DE) .......................... 198 52 928

(51) Int. Cl.⁷ ................................. C08K 9/00
(52) U.S. Cl. ............... 523/202; 424/450; 424/451; 524/205; 524/210
(58) Field of Search ................ 523/202, 205, 523/210; 424/450, 451

(56) References Cited

U.S. PATENT DOCUMENTS

| | | |
|---|---|---|
| 4,622,294 A | 11/1986 | Kung et al. |
| 5,043,158 A | 8/1991 | Sleytr et al. |
| 5,498,421 A | 3/1996 | Grinstaff et al. |
| 5,512,268 A | 4/1996 | Grinstaff et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,665,383 A | 9/1997 | Grinstaff et al. |
| 5,834,556 A | 11/1998 | Desai et al. |

FOREIGN PATENT DOCUMENTS

| | | |
|---|---|---|
| EP | 0 154 620 | 3/1985 |
| EP | 0 199 362 | 10/1986 |

OTHER PUBLICATIONS

Kupeu, S., Sara, M. und Sleytr, U.B. (1995), Biochem. Biophys. Acta, 1235 (2), pp. 263–269. (enclosed).
Caruso, F., Caruso, R.A. und Möhwald, H. (1998), Science, 282, pp. 1111–1113. (enclosed).
G. Hermanson, (1996), Bioconjugate Techniques. (enclosed).
Analytical Biochemistry 76:37 (1976). (enclosed).
Analytical Biochemistry 76:63 (1976). (enclosed).

*Primary Examiner*—Edward J. Cain
(74) *Attorney, Agent, or Firm*—Collard & Roe, P.C.

(57) ABSTRACT

The invention relates to nanocapsules with a size ranging between 50 nm and 10 μm diameter whose envelope layer consists of at least two different, cross-linked polymers P1 and P2. Optionally, a lipid layer may be present underneath said envelope layer. The inventive nanocapsules are produced by covalently cross-linking at least two different water-soluble polymers P1 and P2 on the surface of liposomes. Optionally, the liposomes are dissolved once the polymers are cross-linked. The inventive nanocapsules can carry biologically active compounds.

15 Claims, 1 Drawing Sheet

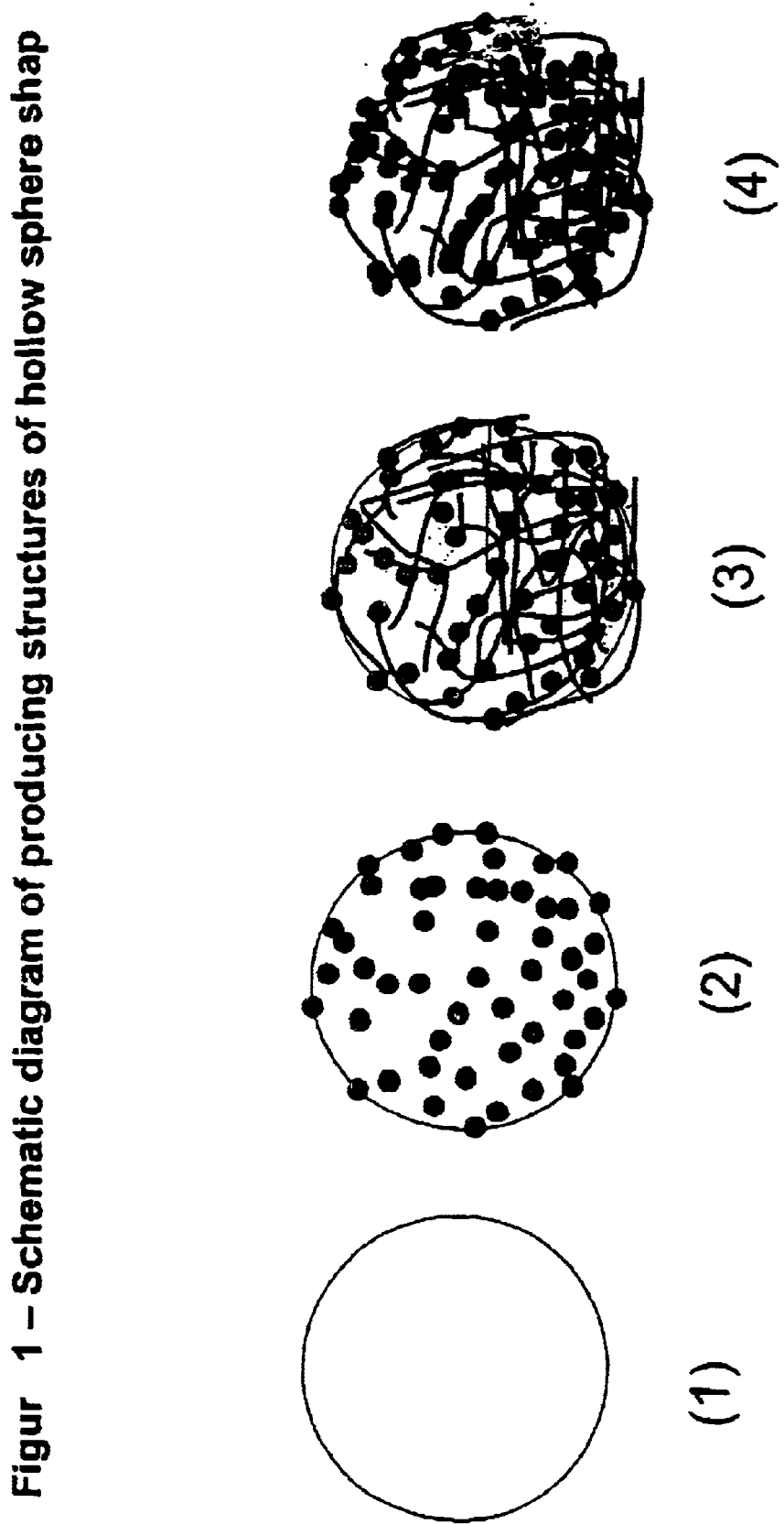
Figur 1 – Schematic diagram of producing structures of hollow sphere shap

NANOCAPSULES AND METHOD OF PRODUCTION THEREOF

CROSS REFERENCE TO RELATED APPLICATIONS

Applicants claim priority under 35 U.S.C. §119 of German Application No.198 52 928.7, filed Nov. 17, 1998. Applicants also claim priority under 35 U.S.C. §120 of PCT/EP99/09744, filed Nov. 15, 1999. The international application under PCT article 21(2) was not published in English.

The invention relates to nanocapsules having a size of between 50 nm and 10 μm in diameter, the coat layer of which consists of at least two different polymers P1 and P2 crosslinked with each other, with a lipid layer optionally being present underneath said coat layer. The nanocapsules of the invention are produced by covalent crosslinking of at least two different water-soluble polymers P1 and P2 on the surface of liposomes, said liposomes optionally being dissolved subsequent to crosslinking. The nanocapsules according to the invention are capable of carrying biologically active compounds.

Nanocapsules or nanoglobules are particulate structures ranging in size between 50 nm and 10 μm, wherein a coat layer separates an inner space from the exterior medium. This property distinguishes nanocapsules from nanospheres; the latter have a uniform cross-section. Structures of similar design are also known in larger dimensions and are then referred to as microcapsules. Liposomes and viral capsides are other related structures of said nanocapsules.

In the preparation of nanocapsules, such methods can be used with advantage, wherein crosslinking reactions are carried out on phase boundary surfaces. The potential benefit of such particles crucially depends on the coat layer used and the preparation method. Well-known coat layers according to prior art are those made up of crosslinked proteins or interfacial polymers, particularly of acrylic acid derivatives.

Coat layers consisting entirely or partially of proteins are of special interest, because they can be designed so as to be biocompatible and degradable. The proteins used in building up are structure-forming, but may also be activity-bearing. Such particles are suitable for the inclusion of foreign substances and in binding other components to the surface. Owing to the natural variety of employable proteins, the surface properties are highly variable and can be adapted to meet various requirements.

Membranes of surface layer (S-layer) proteins have been described in EP 0,154,620). Such membranes are formed by recrystallization of S-layer proteins in free solution or at the surface of liposomes.

In the latter event, previous inclusion of macromolecules is possible, the liposomes undergoing substantial stabilization as a result of establishing the membrane (Kupcu, S., Sara, M., and Sleytr, U. B., Biochem. Biophys. Acta, 1235 (2), 263–269 (1995)). A flat-crystalline build-up of the membranes results in structures having a regular arrangement of homogeneous pores which can be used with advantage in ultrafiltration.

A likewise regular arrangement of chemical groups on the surface results in a highly homogeneous distribution when binding other macromolecules, which is advantageous for use in detection systems. In the event of membranes of S-layer proteins, their immunogenicity may have a limiting effect as to the use in biological systems. S-layer proteins give rise to a strong immune response and are therefore used as adjuvants (U.S. Pat. No. 5,043,158). Moreover, the S-Layer proteins are not activity-bearing themselves.

The U.S. Pat. Nos. 5,498,421; 5,635,207; 5,650,156; 5,665,383; 5,639,473; as well as U.S. Pat. No. 5,512,268 describe the preparation and utilization of hollow spheres ranging in size up to 10 μm, wherein a coat layer is formed at the phase boundary to a non-water-miscible core. Said coat layer is stabilized by disulfide bridges and can be formed of proteins, particularly of hemoglobin or albumin or other thiol-containing polymers. Emulsification of the non-miscible phase is effected using strong ultrasound. During this process, hydrogen peroxide is formed among other things, resulting in oxidative crosslinking of the coat components.

Particles prepared from hemoglobin are capable of absorbing and releasing oxygen, but with a different Hill coefficient as compared to natural hemoglobin. They can be used as blood substitute.

In other uses, gases or contrast agents are entrapped in the particles and employed in medical imaging methods. In still other uses, the enveloping of biologically active substances has been described, provided, they can be dissolved or emulsified in the internal phase without loss of activity. For enveloping hydrophilic macromolecules such as proteins or nucleic acids, this method therefore is suitable to only a limited extent.

Further nanometer range hollow spheres can be prepared by repeated deposition of polyelectrolytes onto colloidally dissolved particles (Caruso, F., Caruso, R. A., and Möhwald, H. (1998) Science 282, 1111–1113). In an example, exceedingly small silica particles are deposited in alternation with poly(diallyldimethylammonium chloride) onto a polystyrene matrix. This matrix can be removed subsequently using calcination or solvents, so that the hollow spheres remain.

The use of liposomes and nanocapsules in the inclusion of biologically active compounds, such as pharmaceutical formulations, is well-known. They are capable of conveying their cargo to the site of action, or release it over a prolonged period of time. The surrounding membrane is capable of protecting the entrapped active substance from degradation or inactivation.

The nature of the entrapped active substance, particularly its solubility and molecular weight can be varied within wide ranges. In addition, owing to their immunological compatibility, liposomes are particularly suitable systems for enveloping pharmaceutically active substances.

Specially designed liposomes can be used to introduce nucleic acids into mammal cells. In an advantageous variant of this technique, lipid-nucleic acid complexes are generated using cationic lipids, and the cells to be treated are transfected with same. The transfection is simple, but proceeds with low efficiency and in a non-specific fashion. In another embodiment, pH-sensitive liposomes are incorporated in the target cells on the endocytotic route. In the acidic compartment of the endosomes, they undergo fusion with the surrounding membrane, conveying their cargo into the interior of the cell on this route. Using this method, even proteins and other active substances can be transported into the interior of the cell.

Liposomes can also be used as detection systems with high signal amplification (U.S. Pat. No. 4,622,294). The signal amplification in this case is achieved as a result of the large number of entrapped enzyme molecules relative to the detected species. One disadvantage in using conventional liposomes is their sensitivity to detergents employed in various uses for suppressing non-specific interactions.

The well-known hollow spheres suffer from the following drawbacks:

The hollow spheres based on the use of S-layers have an aqueous inner space and a well-defined permeability of the coat layer. The potential of enveloping hydrophilic macromolecules is present. However, the restriction of usable compounds to S-layer proteins is disadvantageous. They do not bear activity and exhibit an antigenic effect. The method according to U.S. Pat. No. 5,498,421 and the other above-mentioned documents produces a functional coat layer of proteins at a phase boundary. The system has only limited suitability for entrapping hydrophilic macromolecules. The components of the coat layer are crosslinked with each other in a highly rigid fashion, thereby altering the properties of the hemoglobin being used. Components useful to build up the coat are restricted to such polymers having a plurality of thiol functions and attaching to the phase boundary surfaces being employed.

One disadvantage of conventional liposome systems is their low mechanical and in vivo stability. The particles are incorporated by macrophages of the reticulo-endothelial system within a short time, thereby being removed from the circulation.

It was therefore the object of the invention to provide nanocapsules that would not involve the above-mentioned drawbacks.

According to the invention, this is achieved by means of nanocapsules which have a size of between 50 nm and 10 $\mu$m in diameter and are produced on the surface of liposomes by covalent crosslinking of two different water-soluble polymers P1 and P2 having a plurality of functional groups. The method of producing the nanocapsules of the invention is characterized in that liposomes are produced first, which are coated with a polymer P1 by binding the polymer P1 to the liposome surface in an aqueous solution, and the coated polymer P1 then is covalently crosslinked in an aqueous solution with a polymer P2 which is different from polymer P1, and additional polymer layers are optionally coated by crosslinking.

Liposomes whose size determines that of the nanocapsules formed are employed as starting material. Suitable methods of producing such liposomes are per se known.

One advantageous variant of producing liposomes comprises dissolving the membrane components in ethanol and mixing the solution with water or aqueous buffer solutions. The multi-lamellar liposomes thus obtained are treated in a high-pressure homogenizer (French Press) to produce oligolamellar vesicles of narrow size distribution.

One variant of this technique is passaging the multi-lamellar starting liposomes through isoporous membranes, thereby also resulting in the formation of uni- and oligo-lamellar liposomes of narrow size distribution.

According to another method, uni- and oligo-lamellar liposomes are produced from a detergent-lipid phase by removing the detergent. This can be achieved by gel filtration or dialysis.

According to the invention, the liposomes being used must permit binding of the water-soluble polymer P1. Methods of covalent coupling in aqueous media are known to those skilled in the art (G. Hermanson, Bioconjugate Techniques, Academic Press 1996) and involve heterofunctional or homofunctional linkage of amino, thiol, hydrazo, hydroxy, acidic hydrogen, aldehyde, carboxyl groups or of activated esters thereof in suitable combinations.

Liposomes may include such functional groups. Alternatively, such groups can be generated on the surface of liposomes by chemical modification of lipid components.

Inter alia, suitable membrane-forming or membrane-situated compounds include: phosphatidylethanolamine, phosphatidylserine, phosphatidylglycerol, phosphatidylinositol and derivatives of these compounds, particularly those having a free thiol, amino, carboxyl, active ester, or aldehyde function. Other suitable compounds are amphiphilic molecules having the above-mentioned functional groups, which compounds become incorporated in the lipid layer without destroying same. Among others, these compounds include: alkylamines, alkylthiols and fatty acids, as well as activated esters of fatty acids. Other suitable compounds are sterol derivatives such as cholic acids, deoxycholic acids, thiocholesterol, and similar compounds.

The surface of liposomes can be modified chemically by introducing reactive groups. These include active esters of membrane-situated carboxyl functions, such as N-hydroxysuccinimide esters thereof. These also include aldehyde functions which can be generated by treating membrane-situated amine functions with glutaraldehyde or by oxidation of glycosylated lipids. Furthermore, they include thiol functions which can be generated by reacting membrane-situated amine functions with 2-iminothiolane. In addition, they include membrane-situated 2-pyridyldithionates or maleimide or haloacetyls which can be generated using suitable heterobifunctional reagents.

Advantageously, these reactive groups are generated subsequent to preparing the liposomes, so as to restrict these groups to the outside of the liposomes. When using such reactive groups on membrane-forming or membrane-situated components as early as in the formation of the liposomes, adverse reactions with entrapped cargo molecules are possible in some cases.

Advantageously, homo- or heterofunctional linkage between amino, thiol, hydrazo, aldehyde, carboxyl, active ester, hydroxyl or acidic hydrogen groups is performed with the aid of auxiliary agents. To this end, bifunctional crosslinkers as common in protein chemistry are suitable, such as isothiocyanates, isocyanates, acylazides, N-hydroxysuccinimide esters, sulfonyl chlorides, aldehydes, epoxides, carbonates, imidoesters, carbodiimides, anhydrides, haloacetyls, alkyl halides, maleimides, aziridines, pyridyldisulfides, diazoalkanes, diazoacetyls, carbonyldiimidazoles, N-hydroxysuccinimidylchloroformiates, or compounds containing these functional groups in suitable combinations. A common variant of coupling between amino and carboxyl groups involves derivatizing the carboxyl in a reactive ester, using e.g. N-hydroxysuccinimide. Such derivatizing can be effected on the polymer or on the liposome.

Chelate complexes are suitable for non-covalent coupling, particularly of proteins. Proteins for such coupling can be those forming chelate complexes in a natural way, such as DNA-binding Zn finger proteins. Using recombinant DNA-techniques, it is also possible to insert chelating sequences in proteins. A generally known example are hexahistidine extensions on the N- or C-termini of proteins, known as His-tag. Such proteins are capable of binding to chelating lipid layers in the presence of transition metal ions. The lipid layers can be generated by incorporating amphiphilic compounds containing trinitriloacetic acid or diiminoacetic acid in their polar portion.

No distinct coupling step is necessary if the polymer P1 is a polymer having sufficient affinity to the lipid layer. Suitable polymers P1 therefore include integral and peripheral membrane proteins, but also those polymers whose affinity to the membrane has been increased by subsequent modification. Methods of such modifying include doping of polymers with functionalized alkyl residues, e.g. treatment with N-hydroxysuccinimide esters of long-chain fatty acids, or covalent coupling of phospholipids. Such coupling can be achieved via existing amino, thiol or carboxyl groups with the aid of homo- or heterobifunctional crosslinkers, where the phospholipid is held in solution by means of detergents. Aldehyde functions can be generated on glycosylated proteins by oxidation, which functions can be used in the coupling to lipid-situated amino functions. No auxiliary agent is necessary to this end.

Analogous modifications can also be made on other natural and synthetic polymers.

When admixing amphiphilic comonomers during the preparation of synthetic polymers, the latter may have increased affinity to the membrane.

Molecular-biological procedures can also modify the properties of proteins so as to make them integral or peripheral membrane proteins.

Electrostatic concentrating of P1 at the lipid layer is advantageous in performing the coupling step. To this end, the lipid layer can be doped with suitable ionic components. Suitable components include alkylcarboxylic acids, alkylsulfonic acids, alkylamines, alkylammonium salts, phosphoric acid esters of long-chain alcohols, but also natural or synthetic charged lipids such as phosphatidylglycerol, phosphatidylserine, charged derivatives of phosphatidylethanolamine or cholesterol, phosphatidylinositol, cardiolipin, or sphingolipids.

In the inventive formation of nanocapsules, high polymer loading of the liposomes should be achieved. On the other hand, formation of aggregates must be suppressed as much as possible. If possible, the lipid layer and the polymer therefore should have dissimilar functional groups. Thus, thiol-containing lipid layers can be coated with a variety of thiol-free polymers, and inter alia, with proteins as well which do not have any free thiol function. When using proteins as polymer P1, in particular, this cannot be achieved in any case. Under these circumstances, those heterobifunctional reagents can be used advantageously as auxiliary agents, which allow isolation of stable intermediates enabling a controlled reaction.

Any excess of polymer P1 possibly present after binding can be removed by suitable measures such as dialysis, tangential dialysis, flotation, gel filtration, or ultrafiltration.

In a subsequent step, the polymer P1 is covalently crosslinked by a polymer P2 which is different from polymer P1. The auxiliary agents and procedures employed to this end correspond to those used in covalent fixing of P1. Auxiliary agents are not needed if P1 and P2 are capable of forming covalent compounds by themselves. For example, this is the case when P1 or P2 is a polyfunctional aldehyde and the other reactant is a polyfunctional amine or hydrazine.

Both P1 and P2 are water-soluble polymers having a plurality of functional groups such as amino, carboxyl, thiol, hydrazo, hydroxyl, acidic hydrogen, aldehyde, or active ester groups.

In particular, these include polysaccharides such as alginic acid, chitosan, pectin, hyaluronic acid, polymannuronic acid, heparin, gum arabic, Indian traganth, xanthan gum, Carragheen, locus bean gum, and the salts of these compounds, as well as carboxylated, aminated, thionylated, hydrazylated, or oxidized dextrans, starches, levans, inulins, or agaroses.

Also included are the polymerization product of glutaraldehyde and other polyfunctional aldehydes.

Also included are natural or synthetic proteins or peptides or homo- or heteropolymers of amino acids having multiple free amino, carboxyl or thiol groups.

These include polyacrylic acids, polyacrylamides, polymethacrylic acid, polymethacrylamides, polyvinylpyrrolidones, poly(hydroxyethyl acrylates), poly(hydroxymethyl acrylates), polyethyleneimines and branched poly(ethylene glycols) having multiple free amino, carboxyl or thiol groups. These functional groups can be incorporated by copolymerization or by subsequent modification.

Advantageous variants of producing such copolymers have been described in Hansen (Analytical Biochemistry 76, 37 (1976)) or in O'Connell and Brady (Analytical Biochemistry 76, 63 (1976)), wherein polyacrylamide is polymerized in the presence of biacryls capable of undergoing cleavage. To this end, Hansen uses N,N'-bis(acryloyl)cystamine and subjects the gel having formed to reductive cleavage. An acrylic-based polythiol is formed which is excellently suited for crosslinking in the meaning of the invention. O'Conell and Brady use a bifunctional acrylamide having two vicinal hydroxy functions subsequently subjected to oxidative cleavage. A multivalent aldehyde is formed which can be used to build up crosslinked coat layers.

Also included are mixed forms of the above-mentioned compounds, such as glycosylated proteins, proteins modified following translation, protein complexes with other natural materials, copolymers of sugars and acrylates, and related compounds, provided, all of these compounds are water-soluble and do not form micellar or vesicular structures.

Also included are modified polymers P1 or P2 capable of forming chelate complexes or having affinity to lipid layers.

These include derivatives of the polymers mentioned so far, produced on a chemical route. Also included are those synthetic polymers containing an amphiphilic or a chelating comonomer. Also included are genetically engineered proteins having chelating properties.

One important aspect of use is that one of the polymers P1 or P2 is a protein.

Preferred variants are those where the protein is an albumin, a hemoglobin, a myoglobin, an antibody, $\alpha_2$-macroglobulin, fibrinogen, fibronectin, collagen, vitronectin, protein A, protein G, avidin, streptavidin, concanavalin A, wheat germ agglutinin, or a selectin.

Advantageously, one of the polymers P1 or P2 has a fibrous structure. This is the case in many carbohydrates or in polymers of acrylic acid or derivatives thereof.

The polymer may also have fluorescent properties or acquire such properties by modifications. A suitable substance having such properties is the green fluorescent protein. Other proteins or carbohydrates can be modified using fluorescent substances. Per se, suitable methods are known to those skilled in the art and involve covalent binding of the activated fluorophore to appropriate groups in the polymer, or complex formation of fluorescent metal ions with chelating groups in the polymer. Subsequent modification of nanocapsules with fluorescent substances is also possible.

Free nucleic acids are not included among the suitable polymers.

Since the local concentration of polymer P1 at the surface of the liposomes is much higher than in free solution, crosslinking preferably proceeds at the surface. Residues of P1 in free solution may also be crosslinked with polymer P2 to form particles. Free P2 and free P1–P2 particles can be removed from the coated liposomes by dialysis, tangential dialysis, flotation, gel filtration, or ultrafiltration.

Following coating and crosslinking, hollow spheres are obtained wherein an inner lipid membrane is surrounded by an outer polymer coat. This coat effects a change in the surface properties of the liposomes, increasing their stability.

In a preferred variant of the invention, nanocapsules are produced wherein the liposomes have been dissolved subsequent to crosslinking. Preferably, this can be done by leaching with a detergent.

Such leaching also liberates those polymers P1 or P2 that are bound to the lipid layer only, and not to each other, and also causes decomposition of insufficiently crosslinked structures. The nanocapsules can be separated from the decomposition products by sedimentation, gel filtration or ultrafiltration. Suitable detergents are alkylated sugars such as octylglucoside, salts of cholic acid and its derivatives, alkylsulfonic acids, or polyoxyethylenesorbitols.

In the meaning of the invention, nanometer range hollow spheres are comprised of the two polymers P1 and P2. The shaping liposomes can be allowed to remain or can be removed. The size of the hollow spheres having formed is determined by that of the liposomes initially used.

The nanocapsules described in the present invention are suitable for entrapping biologically active compounds, e.g. pharmaceutical active substances or proteins or nucleic acids.

In this case, liposomes are used which already include the substances to be entrapped. Methods of producing such liposomes are well-known to those skilled in the art. The compounds to be entrapped are limited only in that they must not adversely affect the integrity of the liposomes, as would be the case with detergents. The entrapped compounds remain in the liposomes during the further reaction steps of coating P1 and P2.

The nanocapsules according to the invention can be used to entrap synthetic chemical compounds, proteins, peptides, vitamins, hormones, carbohydrates, or nucleic acids, as well as mixtures thereof, which can be used e.g. as antibiotics, fungicides and antiviral agents, cytostatic agents and immunosuppressive agents, analgetic agents, anesthetics, antidepressive agents, antidiabetic agents, antihypertensive agents, anticoagulants, antiinflammatory agents, anxiolytic, sedative, antiarrhythmic, antiarthritic active substances, bronchodilators, hypoglycemic and hypolipidemic active substances, as well as active substances to stimulate erythropoiesis.

The permeability of the coat layer of the nanocapsules is substantially increased by leaching the liposomes. This process involves the passage of detergent molecules and mixed micelles through the outer coat layer. In the same way, substrates and products of a reaction proceeding in the interior of the nanocapsules can be exchanged. One arrangement for performing such reactions preferably consists of nanocapsules having in their interior enzymatically active substances with high molecular weights, the liposomes of which have been leached by detergents. In particular, suitable substances for such an inclusion are enzymes or ribozymes.

In another variant of this embodiment of the invention, the lipid layer is preserved. In this embodiment, only those substances diffusing through the lipid layer can be exchanged.

In an advantageous embodiment of the invention, those polymers are used to build up the coat layer, which are not only structure-forming, but also, activity-bearing. For example, such coats may have binding properties for other molecules, or catalytic properties. Among proteins are such polymers having structure-forming and activity-bearing properties.

In one variant of this embodiment of the invention, hemoglobin is used to build up the coat structure. The nanocapsules being formed can be used as blood substitute.

In another variant of this embodiment, the coat layer is produced using proteins capable of recognizing and binding frequently occurring characteristics of other proteins. Suitable proteins for this purpose are lectins, biotin-binding or antibody-binding proteins. This variant of the invention produces nanocapsules capable of recognizing glycosylations, antigenic epitopes, or biotin groups on proteins, and of binding these proteins in a highly specific fashion. Such nanocapsules are of interest in biochemical diagnostics. However, nanocapsules having such a structure can also be used in target-controlled application of drugs.

These highly specific molecules therefore include particularly those capable of interacting with the surface of cells. Complementary pairs in this sense are antibodies and membrane-situated antigens, lectins or selecting, and membrane-situated glycosylations, hormones and receptors thereof, and others.

The modular design of these structures is advantageous, allowing the generation of a free number of specificities on just a few coat layers on the one hand, and a highly economic use of the components ultimately determining the specificity, on the other hand.

Moreover, these components do not come in contact with the chemicals used in crosslinking, thereby excluding any risk of inactivation. The valency of the structure that is obtained, i.e., the number of surface-bound specific components can easily be modified by titration. A high density of these components is equivalent to high avidity, enabling stable interactions even in case of unfavorable binding constants of each single interaction, as is the case e.g. between MHC complexes and T-cell receptors.

In another advantageous embodiment of the invention, nanocapsules once formed are modified with additional substances. An important variant of this embodiment is modification of the nanocapsule surface using poly(ethylene glycol). Such coating results in particles having improved compatibility in pharmaceutical uses.

FIG. 1 shows a schematic diagram of producing the nanocapsules of the invention:

Initially, liposomes (1) are coated with polymer P1 (2). Subsequently, this layer is crosslinked by another polymer P2 (3). The shaping liposomes can be removed using detergents (4).

Above all, the nanocapsules according to the invention are used as containers and transporting means for biologically active substances.

In a preferred use, particularly those enzymatically active substances are employed whose substrates and products can be exchanged through the coat layer.

Nanocapsules in the meaning of the present invention have a structure open to diffusion, allowing exchange of molecules of significant size, e.g. during dissolving the lipid layer. However, large molecules such as enzymes are retained by the coat layer. In other inventive uses of the nanocapsules, they are loaded with enzymes catalyzing reactions, the substrates and products of which are capable of passing the coat layer. Compared to the prior art, this way of enveloping a biological macromolecule in nanocapsules offers the advantage of extremely short diffusion paths and an associated increase of the specific activity of the entrapped enzyme. In addition, exposure to crosslinking agents as encountered in chemical fixation can be avoided.

In another application according to the invention, signal-generating systems, such as horseradish-peroxidase or alkaline phosphatase or fluorescence-labelled macromolecules are entrapped in nanocapsules having specific binding properties towards other substances. Such systems are suitable in the detection of said other substances, particularly in medical or biochemical diagnostics. Compared to liposomes, an advantageous fact is that nanocapsules are stable towards detergents, particularly those detergents used to suppress non-specific binding in such procedures, such as Tween 20 or Triton X-100.

In one variant of this use according to the invention, the nanocapsules themselves are the carriers of the signal-generating system. Advantageously, nanocapsules are prepared wherein the polymers have fluorescent properties. To this end, fluorescent derivatives of P1 and/or P2 are used to build up the nanocapsules, or the nanocapsules are coupled covalently with fluorescent substances subsequent to their preparation.

The structures described herein are suitable as vehicles of pharmaceutical active substances in the sense of drug delivery, as a transfer vector, as a sustained release system, or in an enzyme substitution therapy. The invention therefore is also directed to the use of the nanocapsules, produced according to the invention in the manufacture of pharmaceutical formulations which serve in the application of active substances as described above. In another use, i.e., in biochemical diagnostics, the stability of the structure towards detergents represents a substantial advantage, because these substances normally are used to suppress non-specific interactions.

In one inventive use of the nanocapsules, they are designed so as to specifically bind to target cells of mammals. Nanocapsules used in this sense have one or more classes of ligands on their surface, the complementary binding counterparts of which being situated on the surface of the target cells. Nanocapsules having such properties are vehicles of therapeutic agents, directing the latter to a well-defined site of action. In such a use, the inner lipid layer of the hollow spheres can be maintained if beneficial in entrapping the substance to be transported.

In one variant of this use according to the invention, the nanocapsules include substances against which an immune response is to be triggered.

In another advantageous variant of this embodiment of the invention, the nanocapsules are used to transfer active substances into the cytosol of mammal cells. These nanocapsules are designed so as to be incorporated by mammal cells via endocytosis. Nanocapsules used in this embodiment of the invention are comprised of a coat layer which can be digested by the hydrolases of the endosome. Moreover, they are produced using liposomes whose membrane is capable of fusing with that of the endocytotic vesicle. One advantage in this embodiment of the teaching according to the invention is represented by the fact that such a fusion cannot give rise to liberation of lytic endosomal activities into the interior of the cell. Nanocapsules for this purpose can be loaded with various active substances. However, the above-described transportation path is particularly advantageous in the transportation of biological macromolecules incapable of membrane permeation, such as proteins, peptides, antibodies, enzymes, oligonucleotides, DNA, RNA, hormones, but also antibiotics, fungicides and antiviral agents, as well as cytostatic agents.

Nanocapsules in accordance with the present invention are: hydrophilic, permeable and detergent-stable structures made of crosslinked polymers, which can be specified for a large number of applications as a result of the variety of usable components. The present invention provides a substantial expansion in the spectrum of substances that can be used as carrier materials in the sense of drug targeting, as a transfer vector, a sustained release form, or in an enzyme substitution therapy. In this context, the components being used can be both structure-forming and activity-bearing. The hollow spheres described can be produced using substances having an antigenic effect or substances not inducing any immune response.

When using the structure described herein for entrapping enzymes, the architecture open to diffusion ensures high availability of the entrapped activity. In addition, the diffusion paths are extremely short in the selected micrometer and sub-micrometer size ranges. During the preparation of the coats, the entrapped substances are protected against the action of chemical crosslinkers, so that inactivation by these chemicals cannot occur. Therefore, the inclusion of macromolecules as described herein is as mild as possibly conceivable.

EXAMPLES

| | Abbreviations |
|---|---|
| PC | Phosphatidylcholine |
| PS | Phosphatidylserine |
| HEPES | N-[2-Hydroxyethylpiperazine-N'-(2-ethanesulfonic acid)] |
| MES | 2-(N-Morpholino)ethanesulfonic acid |
| Sulfo-SMCC | Sulfosuccinimidyl-4-[N-maleimidomethyl]-cyclohexane-1-carboxylate |
| BSA | Bovine serum albumin |
| EDC | 1-Ethyl-3-(3-dimethylaminopropyl)-carbodiimide |
| CHAPS | 3-[(Cholamidopropyl)dimethylammonio]-2-hydroxypropanesulfonic acid |
| DeoxyBigCHAP | N,N'-Bis(3-gluconamidopropyl)-deoxycholamide |
| EDTA | Ethylenediaminetetraacetic acid |

Example 1

Preparation of BSA-alginate Nanocapsules

Preparation of Liposomes

The liposomes used as matrix are prepared by dialyzing an aqueous mixture of PC (47.5 mole-%), PS (2.5 mole-%) and sodium deoxycholate (50 mole-%). The mixture is dialyzed against 150 mM sodium chloride in water.

Coating With P1

To coat with BSA, the following final concentrations are adjusted: liposomes 4 mg/ml, BSA 10 mg/ml, EDC 10 mg/ml, and MES 50 mM, pH 5.1. Fixation of BSA on the surface of the liposomes proceeds for at least one hour at 37° C., and the reaction subsequently is terminated by adding 200 mM potassium acetate. The excess of employed BSA and EDC is removed by flotation.

Coating with P2

To crosslink the P1 layer, the coated liposomes are added with 200 µg/ml sodium alginate and 50 mM MES buffer, pH 5.1. Crosslinking is initiated by adding 10 mg/ml EDC and performed for two hours at 37° C. The reaction subsequently is terminated as above by adding 200 mM potassium acetate.

Leaching of Liposomes

To remove the liposomes, the coated liposomes are treated with 1% CHAPS. The detergent-stable structures thus obtained correspond to the starting material in size. The efficiency of capsule formation is determined by measuring the light scattering prior to and after detergent addition and is between 30 and 60%.

Example 2

Preparation of Capsules From a Lectin and Alginate

Preparation of Liposomes 820 mg of PC is dissolved in 1 ml of ethanol; 42 mg of PS and 490 mg of sodium deoxycholate are dissolved in 2.5 ml of water. The solutions are combined and filled up with 150 mM NaCl to make 40 ml. This is used to produce liposomes by gel filtration on Sephadex® G-25 in 150 mM NaCl. The liposomes obtained are concentrated by flotation in an ultracentrifuge, treated briefly with ultrasound, and filtrated in a sterile fashion through a filter 0.22 µm in pore size.

Coating With P1

5 ml of the liposomes are added with 1 ml of MES buffer (500 mM, pH 5) and 0.3 ml of NaCl solution (5 mM); subsequently, 35 mg of concanavalin A (SIGMA, type VI) and 75 mg of EDC are added, and the mixture is incubated for 3 hours at 37° C. The reaction is terminated by adding 2 ml of HEPES (1 M, pH 8) and 0.2 ml of potassium acetate solution (5M). The P1-coated liposomes are isolated by flotation in an ultracentrifuge and subsequently taken up in 5 ml of MES buffer (100 mM, pH 5).

Crosslinking With P2

2.5 ml of the liposomes coated with concanavalin A are mixed wit 0.1 ml of sodium alginate (10 mg/ml) and 50 mg of EDC. The solution is filled up with 100 mM MES buffer, pH 5, and 200 mM NaCl to make 4 ml and incubated overnight. To terminate the reaction, 1 ml of HEPES (1 M, pH 8) and 0.2 ml of potassium acetate (5 M), as well as $CaCl_2$ and $MnCl_2$ with 5 µl each (1 M each) are added.

Leaching of liposomes and isolation of the nanocapsules. The batch as above is treated with 2.5 mg of DeoxyBigCHAP. The isolation of the coat structures is achieved by sedimentation in an ultracentrifuge, using a sucrose gradient. Nanocapsules undergo sedimentation through a 0.5 M sucrose layer and are retained at the boundary surface to a 2 M sucrose solution. The samples thus obtained contain no detectable lipid and 1 mg/ml protein. Following incorporation in the coat layer, the concanavalin A being used still can bind and is capable of binding glycosylated proteins.

Example 3

Binding of Glycosylated Proteins to Nanocapsules Made of Concanavalin A-alginate Sec-complex from *Saccharomyces cerevisiae* is purified as described in Panzner et al., Cell 1995, May 19; 81(4), 561–70. 2 . . . 20 µl of the nanospheres from Example 2 and 20 µl of Sec-complex are combined with 80 µl of buffer (50 mM HEPES, pH 7.5, 0.5% DeoxyBigCHAP) and incubated for 12 hours at 4° C. The nanospheres obtained are sedimented (Rotor Beckman 100.3, 75,000 rpm for 30 min) and the distribution of the Sec-complex is analyzed using SDS-PAGE. 5 µl of the nanospheres prepared resulted in binding of more than half of the Sec-complex offered.

Example 4

Inclusion of Peroxidase in Nanocapsules

Liposomes are prepared as in 2. using gel filtration, the starting solution being added with 1 mg/ml horseradish peroxidase (POD). Non-entrapped POD is removed in the flotation. 1.3% of the initial enzyme quantity and 25% of the lipid employed are found in the flotated phase. Coating is effected as in 2., using concanavalin A and alginate. 100 µl of the liposome nanocapsules and 100 µl of non-coated liposomes were used to analyze the inclusion. To this end, both samples were mixed each time with 100 µl of detergent solution (2% DeoxyBIGChap, 100 mM HEPES, pH 7.5, and 150 mM potassium acetate) and added with 350 µl of a sucrose solution of medium density (0.8 M sucrose, 50 mM HEPES, pH 7.5, 150 mM potassium acetate, and 0.2% DeoxyBIGChap) and 100 µl of a sucrose solution of high-density (2 M sucrose, 50 mM HEPES, pH 7.5, 150 mM potassium acetate, and 0.2% DeoxyBIGChap) to form a lower layer in an ultracentrifugation tube (0.8 ml for Beckman SW55), and centrifuged for 1 hour at 55,000 rpm.

Nanocapsules were collected at the phase boundary between 2 M and 0.8 M sucrose, liberated proteins and decomposed coat layers were removed from the uppermost sample application layer. The distribution of protein, lipid and POD for non-coated liposomes and nanocapsules is given in the Table below.

Only after coating the liposomes with concanavalin A and alginate, a significant percentage (about 25%) of POD, together with about 15% of protein, is found in the sedimented phase.

|  | Liposomes, upper phase | Liposomes, lower boundary layer | Nanocapsules, upper phase | Nanocapsules, lower boundary layer |
| --- | --- | --- | --- | --- |
| Lipid distribution | 100% | 0% | 100% | 0% |
| Protein distribution | 97% | 3% | 87.5% | 12.5% |
| POD distribution | 100% | 0% | 73% | 27% |

Example 5

Preparation of BSA-alginate Nanocapsules, Using Thiol-containing Liposomes

Preparation of Liposomes 400 mg of PC and 7.5 mg of octadecylmercaptane are dissolved in 1 ml of ethanol and subsequently placed in 40 ml of buffer (10 mM HEPES, 150 mM NaCl, 5 mM EDTA, pH 7.5) with stirring. The liposome suspension obtained is treated at 800 bar in a high-pressure homogenizer and subsequently pressed through a 0.45 µm filter.

Coating With P1

Liposomes as above are diluted with the specified buffer to make 5 mg/ml lipid. Subsequently, BSA (2 mg/ml) and sulfo-SMCC (2 mM) are added. The mixture is incubated at room temperature overnight.

Crosslinking With P2

0.9 ml of the reaction mixture described is mixed with the following solutions:

0.1 ml of MES buffer, 500 mM, pH 5

0.08 ml of NaCl solution, 5 M 0.1 ml of sodium alginate, 4 mg/ml 0.1 ml of EDC, 100 mg/ml Crosslinking is performed for two hours at room temperature.

Dissolving the Inner Liposomes

Dissolving of the inner liposomes is achieved as illustrated in the previous Examples by adding detergents. With reference to the variation in the intensity of scattered light prior to and after addition of detergent, the formation of coats having intrinsic stability can be deduced. Preferably, 1% sodium cholate is used to dissolve the liposomes.

Example 6

Use of Ionically Charged Liposomes in the Preparation of Nanocapoules

Preparation of Liposomes 400 mg of PC, 7.5 mg of octadecylmercaptane and 9.7 mg of cetyltrimethylammonium bromide are dissolved in 1 ml of ethanol and subsequently placed in 40 ml of buffer (10 mM HEPES, 150 mM NaCl, 5 mM EDTA, pH 7.5) with stirring. The liposome suspension obtained is treated at 800 bar in a high-pressure homogenizer and subsequently pressed through a 0.45 μm filter.

Coating and crosslinking and dissolving the liposomes may be performed as in Example 5. As a result of concentrating the (negatively charged) BSA on the positively charged liposomes, a more rapid reaction is possible, and the reaction time can be reduced to two hours.

Example 7

Nanocapsules From Hemoglobin and Alginate

Preparation of Liposomes 400 mg of PC and 7.5 mg of octadecylmercaptane are dissolved in 1 ml of ethanol and subsequently placed in 40 ml of buffer (10 mM HEPES, 150 mM NaCl, 5 mM EDTA, pH 7.5) with stirring. The liposome suspension obtained is treated at 800 bar in a high-pressure homogenizer and subsequently pressed through a 0.45 μm filter.

Coating With P1

Liposomes as above are diluted with the specified buffer to make 5 mg/ml lipid. Subsequently, hemoglobin (2 mg/ml) and sulfo-SMCC (2 mM) are added. The mixture is incubated at room temperature overnight.

Crosslinking With P2

0.9 ml of the reaction mixture described is mixed with the following solutions:

0.1 ml of MES buffer, 500 mM, pH 5

0.08 ml of NaCl solution, 5 M 0.1 ml of sodium alginate, 4 mg/ml 0.1 ml of EDC, 100 mg/ml Crosslinking is performed for two hours at room temperature.

The intrinsic stability of the coat layer having formed can be deduced as in Example 5 by adding a detergent and measuring the scattered light.

Example 8

Nanocapsules From Hemoglobin and Chitosan

Liposomes are produced as in Example 7 and coated with hemoglobin.

Following completion of coating with hemoglobin, the following solutions are added to 0.9 ml of the reaction mixture described:

0.1 ml of MES buffer, 500 mM, pH 5

0.08 ml of NaCl solution, 5 M 0.08 ml of chitosan from crabs, 85% deacylated, 5 mg/ml 0.1 ml of EDC, 100 mg/ml Crosslinking is performed for two hours at room temperature.

The intrinsic stability of the coat layer having formed can be deduced as in Example 5 by adding a detergent and measuring the scattered light.

Example 9

Nanocapsules Made of Other Proteins and Chitosan

The procedure of Example 8 can be performed under the same conditions using concanavalin A or collagen or albumin.

Example 10

Nanocapsules Made Using an Acrylate

Liposomes are prepared as in Example 5 and coated with BSA.

Preparation of a Thiol-reactive Acrylate

Acrylates having free thiol functions can be produced by reductive decomposition of disulfide-crosslinked polyacrylamide gels. A protocol for the preparation and decomposition of such gels is given in Hansen (Analytical Biochemistry 76, 37–44 (1976)). According to this protocol, thiol-containing polyacrylamides having a substitution level of at least 5% are produced.

Crosslinking With Thiol-reactive Acrylates

Thiol-reactive acrylates as above are added to liposomes coated with proteins as in Example 5 or 7 or 9. The final concentration of the polymer is 400 μg/ml. The mixture is incubated for some hours at room temperature and subsequently, the intrinsic stability of the coat layer can be demonstrated by leaching the liposomes as in Example 5.

Example 11

Nanocapsules Without Use of Proteins

Liposomes are produced as in Example 5.

Coating With P1

Liposomes are diluted with the buffer used in Example 5 to make 5 mg/ml lipid. Subsequently, chitosan (0.25 mg/ml) and sulfo-SMCC (2 mM) are added. The mixture is incubated at room temperature overnight.

Crosslinking With P2

The reaction mixture is added with 400 μg/ml of the thiol-containing polyacrylamide from Example 10. The mixture is incubated for some hours at room temperature and subsequently, the intrinsic stability of the coat layer can be demonstrated by leaching the liposomes as in Example 5.

Coating With a Protein

Example 12

Nanocapsules Made Using Membrane-situated Proteins

Modification of BSA 50 mg of BSA is dissolved in 2.5 ml of buffer (20 mM sodium phosphate, 150 mM NaCl, 40 mM sodium deoxycholate, pH 7.5), followed by addition of 1.25 mg of palmitic acid N-hydroxy-succinimide ester. The mixture is incubated for 2 hours at room temperature, followed by removal of non-bound palmitic acid N-hydroxysuccinimide ester and the hydrolysis products thereof, using gel filtration on Sephadex G25. Here, a buffer as above is used which, however, contains only 4 mM sodium deoxycholate.

Preparation of Liposomes 400 mg of PC is dissolved in 1 ml of ethanol and rapidly diluted in 40 ml of buffer (20 mM sodium phosphate, 150 mM NaCl, pH 7.5). The liposome suspension obtained is treated at 800 bar in a high-pressure homogenizer and subsequently pressed through a 0.45 μm filter.

Coating With Modified BSA

The liposomes are mixed with the modified protein and filled up with buffer (20 mM sodium phosphate, 150 mM Nacl, a pH 7.5) to make 50 ml. Thereafter, sodium deoxycholate is added in an amount so as to make a final concentration of 10 mM. The solution is incubated for two hours at room temperature with gentle agitation, followed by removal of the detergent by dialyzing against 20 mM phosphate, 150 mm NaCl, pH 7.5.

Crosslinking With Alginate

To crosslink the BSA layer, the coated liposomes are added with 200 µg/ml sodium alginate and 50 mM MES buffer, pH 5.1. Crosslinking is initiated by adding 10 mg/ml EDC and performed for two hours at 37° C. The reaction subsequently is terminated by adding 200 mM potassium acetate.

The intrinsic stability of the coat layer can be determined by dissolving the inner lipid layer using a detergent and comparing the intensity of the scattered light.

Example 13

PEG-modified Nanocapsules

Nanocapsules are prepared as in Example 10, using a thiol-containing acrylate. Non-incorporated polymers are removed by flotation, where the buffer used includes 10 mM HEPES, 150 mM NaCl, 5 mM EDTA, pH 7.5. The flotated nanocapsules are added with buffer in an amount so as to make their lipid concentration 5 mg/ml. This solution is added with 0.5 mg/ml α-methoxy-ω-maleimido-polyethyleneglycol and incubated for two hours at room temperature.

Example 14

Fluorescent Nanocapsules

Preparation of Liposomes

All operations are to be performed in a darkened room. 400 mg of PC and 7.5 mg of octadecylmercaptane are dissolved in 1 ml of ethanol and subsequently placed in 40 ml of buffer (10 mM HEPES, 150 mM NaCl, 5 mM EDTA, pH 7.5) with stirring. The liposome suspension obtained is treated at 800 bar in a high-pressure homogenizer and subsequently pressed through a 0.45 µm filter. Calcein not entrapped in the liposomes is removed by gel filtration on Sephadex G25. To this end, a buffer containing 10 mM HEPES, 150 mM NaCl, 5 mM EDTA, pH 7.5, is used.

Coating of the liposomes can be performed as in Example 5. In this Example, calcein was entrapped at a concentration resulting in self-quenching of the emitted fluorescent light. This quenching effect is cancelled when calcein exits into the surrounding medium. Such nanocapsules can be used in the determination of stabilities in various media, particularly in biological systems such as stomach contents, intestine contents, serum, and lymph.

I claim:

1. A method of producing nanocapsules having a diameter of from 50 nm to 10 µm, diameter characterized in that liposomes are produced which are coated with a polymer P1 by binding the polymer P1 to the liposome surface in an aqueous solution, and the coated polymer P1 then is covalently crosslinked in an aqueous solution with a polymer P2 which is different from polymer P1, and additional polymer layers are optionally coated by crosslinking.

2. The method according to claim 1, characterized in that the liposomes are dissolved subsequent to crosslinking the polymers, preferably by leaching with a detergent.

3. The method according to claim 1, characterized in that liposomes are used as starting material which carry biologically active compounds or compounds of a detection system, which compounds remain in the nanocapsules when performing the method.

4. The method according to claim 1, characterized in that those polymers are used as water-soluble polymers P1 and P2 which have amino, carboxyl, thiol, hydrazo, hydroxy, acidic hydrogen, aldehyde and/or active ester groups or combinations of these groups as functional groups, and which do not themselves undergo formation of micellar or vesicular structures.

5. The method according to claim 1, characterized in that auxiliary agents are used to crosslink polymer P1 with the liposomes or polymer P1 with polymer P2.

6. The method according to claim 5, characterized in that isothiocyanates, isocyanates, acylazides, N-hydroxysuccinimide esters, sulfonyl chlorides, aldehydes, epoxides, carbonates, imidoesters, carbodiimides, anhydrides, haloacetyls, alkyl halides, maleimides, aziridines, pyridyldisulfides, diazoalkanes, diazoacetyls, carbonyldiimidazoles, N-hydroxysuccinimidylchloroformiates, or compounds containing these functional groups in suitable combinations are used as auxiliary agents.

7. The method according to claim 1, characterized in that the water-soluble polymers P1 or P2 have chelating or chelate-binding properties.

8. The method according to claim 1, characterized in that the polymers P1 and/or P2 are proteins.

9. The method according to claim 1, characterized in that the polymers P1 and/or P2 are carbohydrates.

10. The method according to claim 1, characterized in that the water-soluble polymers P1 and/or P2 are synthetic polymers.

11. The method according to claim 1, characterized in that the nanocapsules obtained are modified at their surface, preferably using poly(ethylene glycol), proteins, peptides, or hormones, with poly(ethylene glycol) being particularly preferred.

12. Nanocapsules, produced according to claim 1.

13. Nanocapsules having a diameter of from 50 nm to 10 µm, characterized in that the coat layer thereof is comprised of at least two different polymers P1 and P2 crosslinked with each other.

14. Use of the nanocapsules according to claim 1 in the production of pharmaceutical formulations used in the application of active substances.

15. Use of the nanocapsules according to claim 1 in biochemical diagnostics.

* * * * *